US010428397B2

(12) United States Patent
Dumesic et al.

(10) Patent No.: US 10,428,397 B2
(45) Date of Patent: *Oct. 1, 2019

(54) METHOD TO PRODUCE WATER-SOLUBLE SUGARS FROM BIOMASS USING SOLVENTS CONTAINING LACTONES

(71) Applicant: WISCONSIN ALUMNI RESEARCH FOUNDATION, Madison, WI (US)

(72) Inventors: James A. Dumesic, Verona, WI (US); Jeremy S. Luterbacher, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/635,354

(22) Filed: Jun. 28, 2017

(65) Prior Publication Data
US 2017/0298458 A1 Oct. 19, 2017

Related U.S. Application Data

(63) Continuation of application No. 14/692,018, filed on Apr. 21, 2015, now Pat. No. 9,725,776, which is a continuation of application No. 13/736,550, filed on Jan. 8, 2013, now Pat. No. 9,045,804.

(51) Int. Cl.
| C13K 1/00 | (2006.01) |
| C13K 1/02 | (2006.01) |
| C07D 307/50 | (2006.01) |
| C07H 3/06 | (2006.01) |
| C13K 1/06 | (2006.01) |
| C13K 13/00 | (2006.01) |
| C07D 307/46 | (2006.01) |

(52) U.S. Cl.
CPC ............ *C13K 1/02* (2013.01); *C07D 307/46* (2013.01); *C07D 307/50* (2013.01); *C07H 3/06* (2013.01); *C13K 1/00* (2013.01); *C13K 1/06* (2013.01); *C13K 13/002* (2013.01)

(58) Field of Classification Search
CPC . C13K 1/002; C13K 1/02; C13K 1/06; C13K 1/00; C07D 307/45; C07D 307/50; C07H 3/06

See application file for complete search history.

(56) References Cited

U.S. PATENT DOCUMENTS

| 9,045,804 | B2* | 6/2015 | Dumesic | ............... C13K 1/02 |
| 9,725,776 | B2* | 8/2017 | Dumesic | ............... C13K 1/02 |
| 2010/0324310 | A1 | 12/2010 | Dumesic et al. | |
| 2012/0302766 | A1 | 11/2012 | Dumesic et al. | |

FOREIGN PATENT DOCUMENTS

WO WO2008/053206 A2 5/2008

OTHER PUBLICATIONS

Alonso, D.M., Wettstein, S.G., Mellmer, M.A., Gurbuz, E.I. & Dumesic, J. A., Integrated conversion of hemicellulose and cellulose from lignocellulosic biomass. *Energy Environ. Sci.* (2013). doi:10.1039/C2EE23617.
Binder, J. B. & Raines, R..T., Fermentable sugars by chemical hydrolysis of biomass. *Proceedings of the National Academy of Sciences* 107, 4516-4521 (2010).
Bobleter, O., Hydrothermal Degradation of Polymers Derived From Plants. *Progress in Polymer Science* 19, 797-841 (1994).
Fegyverneki, Daniel, et al., Gamma-valerolactone-based solvents, Tetrahedron, 2010, pp. 1078-1081, vol. 66, Elsevier, journal homepage: www.elsevier.com/locate/tet.
Gürbüz, E.I., Alonso, D. M., Bond, J. Q. & Dumesic, J. A., Reactive extraction of levulinate esters and conversion to gamma-valerolactone for production of liquid fuels. *ChemSusChem* 4, 357-361 (2011).
Gürbüz, E.I. et al., Conversion of Hemicellulose into Furfural Using Solid Acid Catalysts in γ-Valerolactone. *Angewandte Chemie International Edition* n/a-n/a (2012).doi:10.1002/anie.201207334.
Hodge, D.B., Karim, M.N., Schell, D.J. & McMillan, J.D., Soluble and insoluble solids contributions to high-solids enzymatic hydrolysis of lignocellulose. *Bioresour. Technol.* 99, 8940-8948 (2008).
Houghton, J., *Breaking the biological barriers to cellulosic ethanol: A joint research agenda.* (US Department of Energy, 2005), at http://www.doegenomestolife.org/biofuels (2005).
Lange, J.P., Van Der Heide, E., Van Buijtenen, J. & Price, R., Furfural—A Promising Platform for Lignocellulosic Biofuels. *ChemSusChem* 5, 150-166 (2012).
Lee, Y.Y., Iyer, P. & Torget, R.W. In *Recent Progress in Bioconversion of Lignocellulosics* (Tsao, P. D. G. T. et al.) 93-115 (Springer Berlin Heidelberg, 1999).at http://link.springer.com/chapter/10.1007/3-540-49194-5_5 (1999).
Liu, C.G. & Wyman, C.E., The effect of flow rate of very dilute sulfuric acid on xylan, lignin, and total mass removal from corn stover. *Industrial & Engineering Chemistry Research* 43, 2781-2788 (2004).
Lynd, L.R. et al. How biotech can transform biofuels. *Nat. Biotech.* 26, 169-172 (2008).
Pagán-Torres, Y. J., Wang, T., Gallo, J. M. R., Shanks, B. H. & Dumesic, J. A., Production of 5-Hydroxymethylfurfural from Glucose Using a Combination of Lewis and Brønsted Acid Catalysts in Water in a Biphasic Reactor with an Alkylphenol Solvent. *ACS Catal.* 2, 930-934 (2012).

(Continued)

*Primary Examiner* — David M Brunsman
(74) *Attorney, Agent, or Firm* — Joseph T. Leone, Esq.; DeWitt LLP

(57) ABSTRACT

A process to produce an aqueous solution of carbohydrates that contains C6-sugar-containing oligomers, C6 sugar monomers, C5-sugar-containing oligomers, C5 sugar monomers, or any combination thereof is presented. The process includes the steps of reacting biomass or a biomass-derived reactant with a solvent system including a lactone and water, and an acid catalyst. The reaction yields a product mixture containing water-soluble C6-sugar-containing oligomers, C6-sugar monomers, C5-sugar-containing oligomers, C5-sugar monomers, or any combination thereof.

17 Claims, 7 Drawing Sheets

(56) References Cited

OTHER PUBLICATIONS

Peterson, A.A. et al., Thermochemical biofuel production in hydrothermal media: A review of sub- and supercritical water technologies. *Energy Environ. Sci.* 1, 32-65 (2008).
Ragauskas, A.J. et al. The Path Forward for Biofuels and Biomaterials. *Science* 311, 484-489 (2006).
Roman-Leshkov, Y., Chheda, J.N. & Dumesic, J.A., Phase modifiers promote efficient production of hydroxymethylfurfural from fructose. *Science* 312, 1933 (2006).
Roman-Leshkov, Y., Barrett, C.J., Liu, Z.Y. & Dumesic, J.A., Production of dimethylfuran for liquid fuels from biomass-derived carbohydrates. *Nature* 447, 982-985 (2007).
Sanderson, K., Lignocellulose: A chewy problem. *Nature* 474, S12 (2011).
Shill, K. et al., Ionic liquid pretreatment of cellulosic biomass: Enzymatic hydrolysis and ionic liquid recycle. *Biotechnology and Bioengineering* 108, 511-520 (2011).
Sluiter, A. et al., Determination of sugars, byproducts, and degradation products in liquid fraction process samples. (National Renewable Energy Laboratory (2004).
Somerville, C., The Billion-Ton Biofuels Vision. *Science* 312, 1277 (2006).
Van Dam et al., "The conversion of fructose and glucose in acid media: formation of hydroxymethylfurfural", Starch, 38 (1986), pp. 95-101.
Von Sivers, M. & Zacchi, G., A techno-economical comparison of three processes for the production of ethanol from pine. *Bioresource Technology* 51, 43-52 (1995).
Wettstein, S.G., Alonso, D.M., Chong, Y. & Dumesic, J.A., Production of levulinic acid and gamma-valerolactone (GVL) from cellulose using GVL as a solvent in biphasic systems. *Energy Environ. Sci.* 5, 8199-8203 (2012).
Wilson, D.B., Cellulases and biofuels. *Current opinion in biotechnology* 20, 295-299 (2009).

* cited by examiner

FIG. 1A
FIG. 1B
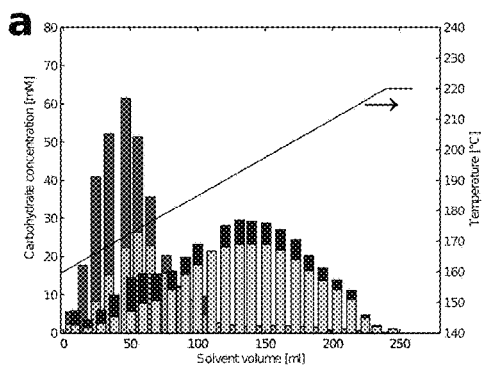
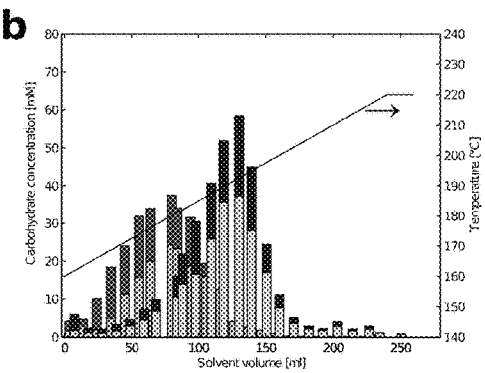
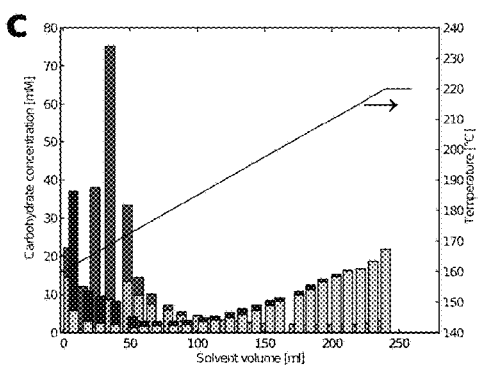
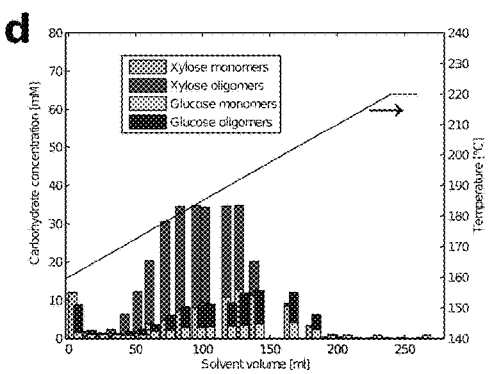
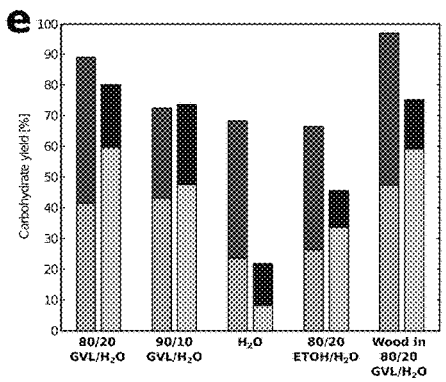
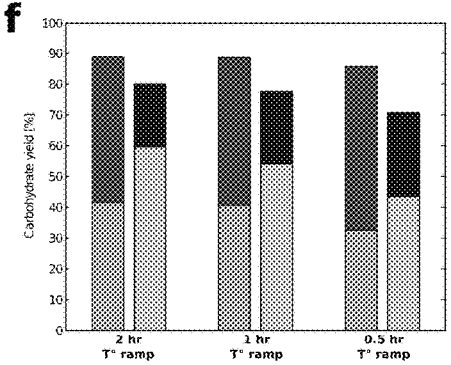
FIG. 1C (middle)
FIG. 1D (middle)
FIG. 1E (bottom)
FIG. 1F (bottom)

METHOD TO PRODUCE WATER-SOLUBLE SUGARS FROM BIOMASS USING SOLVENTS CONTAINING LACTONES

CROSS-REFERENCE TO RELATED APPLICATIONS

This is a continuation of co-pending application Ser. No. 14/692,018, filed Apr. 21, 2015, which is a continuation of application Ser. No. 13/736,500, filed Jan. 8, 2013 (now U.S. Pat. No. 9,045,804, issued Jun. 2, 2015).

FEDERAL FUNDING STATEMENT

This invention was made with government support under DE-FC02-07ER64494 awarded by the Department of Energy. The government has certain rights in the invention.

BACKGROUND

Successful carbohydrate recovery from lignocellulosic biomass requires breaking intermolecular bonds in glucan and xylan chains while avoiding further reaction of the resulting glucose and xylose[9]. However, in neutral or dilute aqueous acid solutions (<10 wt % mineral acid systems), the resulting glucose further reacts to yield furans or other degradation products. The glucose degradation reactions significantly outpace cellulose depolymerization at temperatures below 250-350° C. depending on the acid content. This leads to the need for reaction systems with short residence times (10 ms to 1 min) at high temperatures (250-400° C.) in order to obtain a high selectivity to glucose at high conversion[9,10], while minimizing degradation of the desired glucose product. These types of short residence time reactions are especially impractical when using heterogeneous starting products such as biomass. Higher yields are obtainable at lower temperatures and longer residence times using increased homogeneous catalyst concentrations such as high mineral acid concentrations and/or ionic liquids[5,8]. However, in both cases, the homogeneous catalyst is a very significant expense. Thus, recovering the catalyst is critical for the commercial viability of these processes. Ultimately, recovering and recycling the catalysts ends up being a significant component of the processing costs[5,8,11]. Cellulase enzymes operating at only 50° C. can achieve near complete conversion of cellulose. However, in these processes, the cellulose must be rendered accessible by a thermochemical pretreatment of the raw cellulosic feed stock. Both enzyme and pretreatment costs are significant obstacles toward the successful commercialization of these processes. For example, enzyme costs are consistently shown to account for between US $0.50 and $2.00 per gallon of ethanol (2009 dollars), a significant portion of the overall cost of production. See, for example, Heather L MacLean and Sabrina Spatari 2009 *Environ. Res. Lett.* 4 014001 and David B Wilson 2009 *Curr Opin Biotechnol* Volume 20, Issue 3, Pages 295-299.

Strategies have been developed to successfully produce glucose and xylose from biomass while avoiding further degradation despite using low catalyst concentration and low temperature. One such strategy involves flowing a solvent through a heated packed bed of biomass in a flow-through reaction system. This approach decouples the residence times of the solid carbohydrate polymer from its soluble counterpart[12,13]. These systems are typically limited by their ability to produce reasonably concentrated product solutions. Indeed, using an aqueous solution of 1 wt % $H_2SO_4$ as the extraction solvent, glucose yields of only 45-55% are achieved when using a 2-4 wt % sugar solution as the feedstock[12].

In recent work, GVL-water solutions coupled with very dilute acid concentrations (>0.1 M $H_2SO_4$) or solid acid catalysts have shown the ability to solubilize lignocellulosic biomass and promote dehydration of glucose to levulinic acid and of xylose to furfural[14-16].

SUMMARY OF THE INVENTION

Disclosed and claimed herein is a process to produce an aqueous solution of carbohydrates comprising C6-sugar-containing oligomers, C6-sugar monomers, C5-sugar-containing oligomers, C5-sugar monomers, or any combination thereof. The process comprises reacting biomass or a biomass-derived reactant with a solvent system comprising (i) an organic solvent selected from the group consisting of beta-, gamma-, and delta-lactones, and combinations thereof, and (ii) at least about 1 wt % water; in the presence of an acid catalyst for a time and under conditions to yield a product mixture wherein at least a portion of water-insoluble C6-sugar-containing polymers or oligomers, or water-insoluble C5-sugar-containing polymers or oligomers, if present in the biomass or biomass-derived reactant, are converted to water-soluble C6-sugar-containing oligomers, C6-sugar monomers, C5-sugar-containing oligomers, C5-sugar monomers, or any combination thereof. Optionally, a solute is added to the product mixture in an amount sufficient to cause partitioning of the product mixture into an aqueous layer and a substantially immiscible organic layer. The water-soluble products partition into the aqueous phase where they can be recovered, concentrated, purified, and/or further upgraded, with or without any intervening treatment steps.

Thus, included within the scope of the claims is a process to produce an aqueous solution comprising glucose oligomers, glucose monomers, xylose oligomers, xylose monomers, or any combination thereof. The process comprises reacting biomass or a biomass-derived reactant with a solvent system comprising (i) an organic solvent selected from the group consisting of beta-, gamma-, and delta-lactones, and combinations thereof, and (ii) at least about 1 wt % water. The solvent system also includes an acid catalyst. The reaction is conducted for a time and under conditions to yield a product mixture wherein at least a portion of water-insoluble glucose-containing polymers or oligomers, or water-insoluble xylose-containing polymers or oligomers, if present in the biomass or biomass-derived reactant, are converted to water-soluble glucose oligomers, glucose monomers, xylose oligomers, xylose monomers, or any combination thereof. In an optional second step, a non-reactive solute is added to the product mixture in an amount sufficient to cause partitioning of the product mixture into an aqueous layer and a substantially immiscible organic layer. The product carbohydrates are contained in the aqueous layer. The lactone is present in the organic layer and can be recycled.

Preferably the organic solvent is miscible with water, or can dissolve from 2 wt % to 25 wt % water. The method can be conducted using gamma-valerolactone (GVL) as the organic solvent. As noted below, the organic solvent may be present in a ratio with water (organic solvent:water) selected from the group consisting of about 60:40, about 65:35, about 70:30, about 75:25, about 80:20, about 85:15, about 90:10, about 95:5, about 97:3, about 98:2, and about 99:1.

The acid catalyst used in any embodiment of the method may be homogeneous or heterogeneous. If the acid catalyst is homogeneous, preferably it is present in a concentration not greater than 100 mM based on volume of the solvent system. If the acid catalyst is heterogeneous, preferably it is present in a concentration not greater than 1.0 wt % based on weight of the solvent system. In any embodiment of the method, the acid catalyst may be a mineral acid, a solid acid catalyst selected from the group consisting of solid Brønsted acid catalysts, solid Lewis acid catalysts, and combinations thereof, a heteropolyacid, a mesoporous silica, or a zeolite.

If a solute is used to partition the product mix, the solute used to drive partitioning of the product mixture is preferably a water-soluble, inorganic salt (although any non-reactive solute that drives the partitioning may be used). Sodium chloride is the preferred solute. As shown in FIGS. 2A and 2B there is a tradeoff in product composition depending on how much solute is added to the product mixture. For example, when using NaCl as the solute, a relatively lower salt content of about 4 wt % aq results in a very high concentration of sugars in the product mixture, but only about 50% of the sugars in the biomass reactant are recovered. This approach, however, would be preferred if a product having a high concentration of sugars is desired. In contrast, adding 12 wt % aq NaCl to the product mixture (closer to saturation) about 90% of the sugars present in the initial mixture are recovered, but are present in a lower concentration in the aqueous phase. Either approach is equally preferred because certain upgrading processes will function better with a solution having a high carbohydrate concentration. Other upgrading processes will perform well with a solution that has a more dilute sugar concentration, in which more of the sugars have been recovered.

The reaction with the solvent system may be conducted at any temperature, but preferably is conducted at a temperature range selected from the group consisting of from about 100° C. to about 300° C., about 140° C. to about 240° C., and about 150° C. to about 200° C.

In all reactions described herein, the ratio of lactone-to-water is preferably at least about 60 wt % lactone (and increasing) to about 40 wt % lactone (and decreasing) (60:40; lactone:water). Thus, explicitly included within the disclosed process are ratios of lactone-to-water of 60:40, 65:35, 70:30, 75:25, 80:20, 85:15, 90:10, 95:5, 97:3, 98:2, 99:1, and any ratio that falls between the two extremes.

Any beta, gamma, or delta lactone, derived from any corresponding C4 to C16 carboxylic acid may be used in the process. Gamma-lactones and delta-lactones are preferred. C5 to C12 gamma-lactones are more preferred still. Gamma-valerolactone is most preferred.

The process may be carried out in a continuous fashion or batch-wise. The process may be carried out at any temperature and pressure. However, for economic viability, it is preferred that the reaction be carried out at a temperature of from about 100° C. to about 300° C., more preferably from about 140° C. to about 240° C., and more preferably still from about 150° C. to about 200° C. The reaction may be conducted at a static temperature, using any suitable temperature ramp, non-linear temperature change or combination thereof. Conducting the process at temperatures above and below these preferred ranges is explicitly within the scope of the process as recited in the claims, unless the claims explicitly recite temperature limitations.

Residence time of the solvent in the reactor may vary at the choice of the user, and be adjusted empirically based on the selection of the biomass or biomass-derived reactant. Generally, though, it is preferred that the solvent have a residence time in the reactor of from 1 min to 24 hours. Residence times above and below these extremes are within the scope of the process. Thus, the process explicitly covers residence times selected from the group consisting of 1 min to 24 hours, 1 min to 20 hours, 1 min to 12 hours, 1 min to 6 hours, 1 min to 3 hours, 1 min to 2 hours, 1 min to 1 hour, and 1 min to 30 min.

The reaction solvent comprises one or more lactones, water, and an acid. The acid may be a homogeneous acid, a heterogeneous acid, a Brønsted-Lowry acid, a Lewis Acid, a solid acid, a mineral acid, or any combination of these. (Note that any given acid might be described by more than one of the foregoing identifiers.) If homogeneous, the acid is present in dilute concentration, preferably no greater than about 100 mM. Thus, acid concentrations between about 0.1 mM and about 100 mM are preferred, more preferably between about 1 mM and about 50 mM, and more preferably still between about 1 mM and about 25 mM. On a weight percentage basis, based on the weight of the lactone/water solvent, the acid is preferably present in an amount of about 0.001 wt % to about 1.0 wt %, more preferably from about 0.01 wt % to about 0.1 wt %.

BRIEF DESCRIPTION OF THE DRAWINGS

FIGS. 1A, 1B, 1C, 1D, 1E, and 1F: Fractionation results for various solvents. All experiments were performed with corn stover unless otherwise specified. All solutions contained 5 mM $H_2SO_4$. The solid line in FIGS. 1A, 1B, and 1C represents the increasing temperature within the reactor during fractionation. The legend is shown in FIG. 1D. FIG. 1A: Carbohydrate concentration as a function of solvent volume for 80 wt % GVL to 20 wt % water. FIG. 1B: Carbohydrate concentration as a function of solvent volume for 90 wt % GVL to 10 wt % water. FIG. 1C: Carbohydrate concentration as a function of solvent volume for water. FIG. 1D: Carbohydrate concentration as a function of solvent volume for 80 wt % GVL to 20 wt % ethanol. FIG. 1E: Total soluble carbohydrate yields using various solvent systems. FIG. 1F: Total soluble carbohydrate yield as a function of the time span of the temperature ramp.

FIG. 2A: Results for 80 wt % GVL to 20 wt % water. FIG. 2B: Results for 90 wt % GVL to 10 wt % water. Salt content is given as the mass fraction of the total amount of water present. FIG. 2C: Effect of fraction removal and temperature ramp time shortening. For the results marked by with *, fractions containing less than a total of 3% of the total carbohydrates were removed.

FIG. 3A: Monomer production from the separated aqueous phase as a function of residence time at 413 K. Separated aqueous phase was treated unchanged. FIG. 3B: Furan production from soluble carbohydrate as a function of residence time at 443 K. Separated aqueous phase, to which 100 mM $AlCl_3$ was added, was treated in the presence of a 2-sec-butylphenol (SBP) organic layer. Yields reported were calculated based on the analysis of both phases. Sugars were measured only in the aqueous phase and 94-100% of furans were recovered in SBP.

FIG. 5A: Corn stover extracted with an 80 wt % GVL to 20 wt % water mixture. FIG. 5B: Corn stover extracted with a 90 wt % GVL to 10 wt % water mixture.

FIG. 6A: Cumulative yield obtained with an 80 wt % GVL to 20 wt % water solution. FIG. 6B: Cumulative yield obtained with a 90 wt % GVL to 10 wt % water solution. FIG. 6C: Cumulative yield obtained with water. FIG. 6D: Cumulative yield obtained with an 80 wt % ethanol to 20 wt % water solution.

FIG. 7A: Results for 80 wt % GVL to 20 wt % water. FIG. 7B: Results for 90 wt % GVL to 10 wt % water.

DETAILED DESCRIPTION

Abbreviations and Definitions

Figures 2A, 2B, 2C:
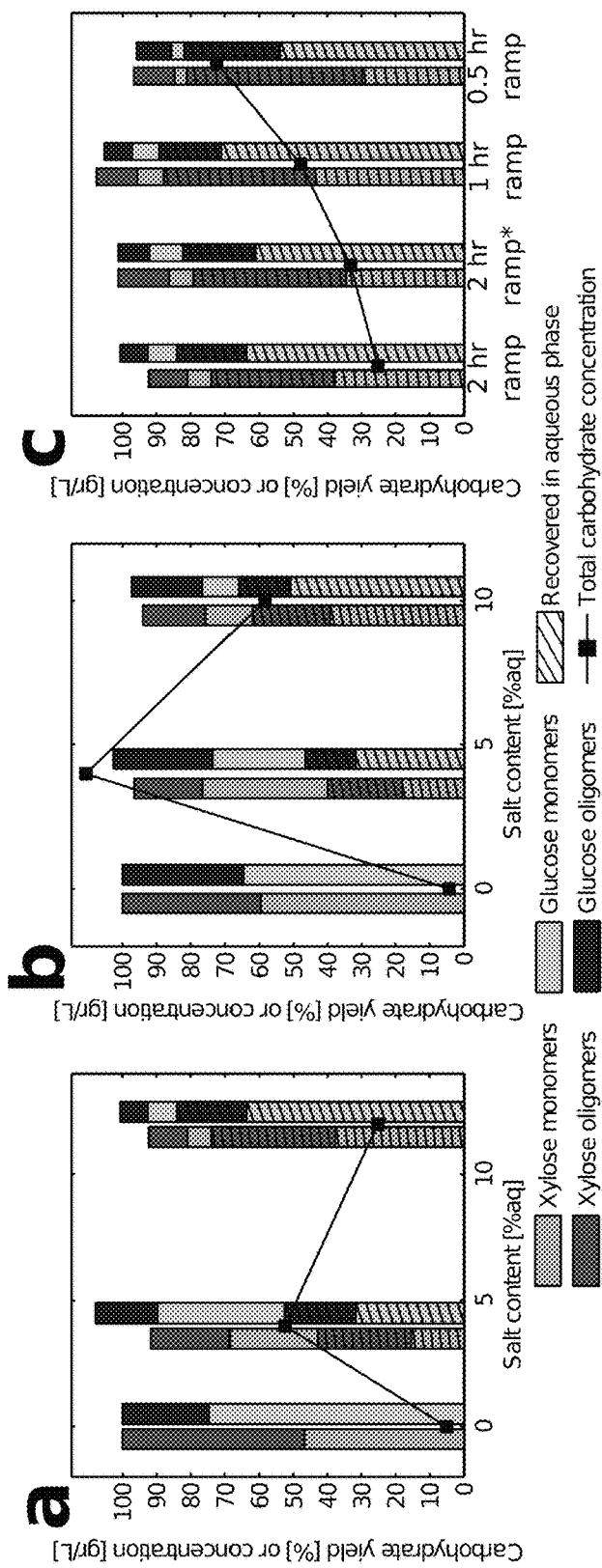
FIGS. 2A, 2B, and 2C: Aqueous phase separation and carbohydrate recovery from GVL/water mixtures using NaCl. Stacked bars represent fractions of the total carbohydrate yield. The solid line represents the total mass concentration of sugars in solution.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose. For the experiments described below, dried corn stover was obtained through the Great Lakes Bioenergy Research Center, Madison, Wis., USA. Dried maple wood was obtained from Mascoma corporation, Hanover, N.H.

"Glucose-containing oligomers, glucose-containing polymers, Glucose-containing reactant, C6-containing reactant"=Any chemical species, having any type of intramolecular bond type, that comprises a glucose or other C6 sugar unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates and other polymers and carbohydrates containing C6 sugar units, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose, including those found in biomass, are explicitly included within the definition. Likewise, "xylose-containing oligomers, xylose-containing polymers, xylose-containing reactant, C5-containing reactant"=Any chemical species, having any type of intramolecular bond type, that comprises a xylose or other C5 sugar unit.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (⁻3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Homogeneous catalyst"=A catalyst that exists in the same phase (solid, liquid, or gas) as the reactants under reaction conditions.

"Heterogeneous catalyst"=A catalyst that exists in a different phase than the reactants under reaction conditions.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding C4 to C16 carboxylic acid. Thus, as used herein, the term "lactone" explicitly includes (without limitation) unsubstituted and substituted beta- and gamma-butyrolactone and beta-, gamma-, and delta-valerolactones to beta-, gamma, and delta-hexadecalactones. Some lactones are miscible in water, such as GVL; other lactones have more limited solubility in water. Those lactones that can dissolve at least about 1 wt % water, and more preferably at least about 5 wt % (or more) of water (up to miscible) are suitable for use in the process described herein. Gamma- and delta-lactones are preferred. Gamma-valerolactone is most preferred.

Mineral acid=any mineral-containing acid, including (by way of example and not limitation), hydrochloric acid, nitric acid, phosphoric acid, sulfuric acid, boric acid, hydrofluoric acid, hydrobromic acid, and the like.

Organic acid=any organic acid, without limitation, such as toluenesulfonic acid, formic acid, acetic acid, trifluoroacetic acid, oxalic acid, and the like.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lanthanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, $(alkyl)AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lanthanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

The term "solute" is broadly defined herein to include any non-reactive salt (such as NaCl, NaBr, and any other inorganic or organic salts) or other non-reactive organic or inorganic solutes that drive the formation of an aqueous layer and a substantially immiscible organic layer containing the lactone when the solute is added to the product mixture after reaction. Sodium salts are preferred. Sodium chloride is also preferred.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

The Process:

The process yields an aqueous solution of carbohydrates, selectively and with minimal degradation of carbohydrate monomers. The process comprises reacting biomass or a biomass-derived reactant with a solvent system comprising (i) an organic solvent selected from the group consisting of beta-, gamma-, and delta-lactones, and combinations thereof, and (ii) at least about 1 wt % water. The solvent system also includes an acid catalyst. The reaction is conducted for a time and under conditions to yield a product mixture wherein at least a portion of water-insoluble glucose-containing polymers or oligomers, or water-insoluble xylose-containing polymers or oligomers, if present in the biomass or biomass-derived reactant, are converted to water-soluble glucose oligomers, glucose monomers, xylose oligomers, xylose monomers, or any combination thereof. Optionally, a non-reactive solute is added to the product mix in an amount sufficient to cause partitioning of the product mixture into an aqueous layer and a substantially immiscible organic layer. The product carbohydrates are contained in the aqueous layer. The lactone is present in the organic layer and can be recycled.

Figure 4:
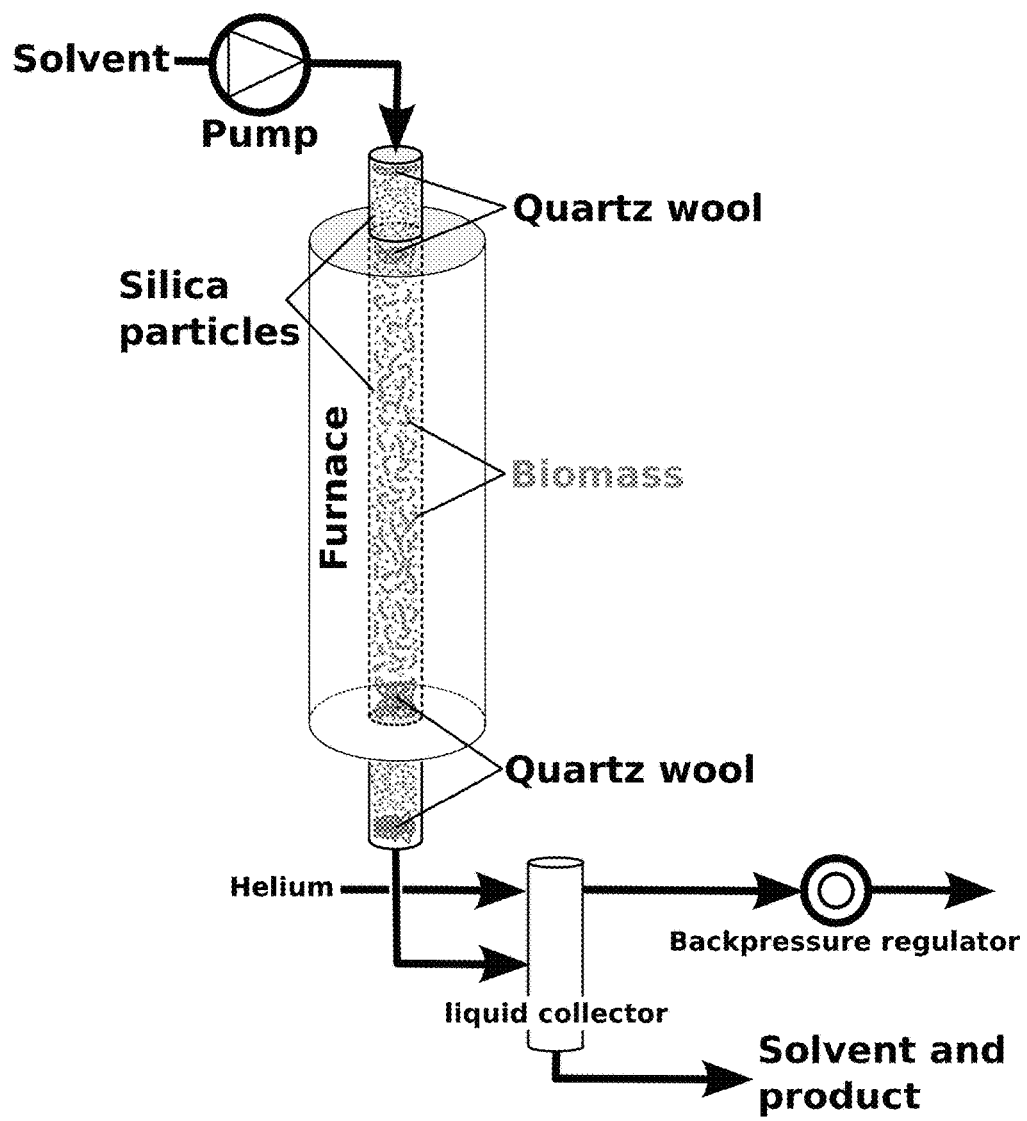
FIG. 4: Schematic diagram of the flow-through reactor used in the Examples.

In FIGS. 1A and 1B, fraction carbohydrate concentration results as a function of solvent volume flowed through the reactor depicted in FIG. 4 are shown for reaction solvents containing 80 wt % GVL to 20 wt % water mixtures (80/20 GVL, FIG. 1A) and 90 wt % GVL to 10 wt % water (90/10 GVL, FIG. 1B), respectively. (See Examples for full experimental details.) Both solutions contained 5 mM $H_2SO_4$ (~0.05 wt %). In both cases, C5 (xylose and xylo-oligomer) and C6 (glucose and gluco-oligomer) fraction concentrations reach maxima between about 160° C. and about 200° C. and then decrease at higher temperatures. Equivalent results obtained with water as a solvent show a significantly different behavior, with glucose concentration continuously increasing with increasing temperature up to 493 K and potentially beyond. See FIG. 1C. This result indicates that GVL promotes cellulose deconstruction and hydrolysis with most cellulose hydrolysis occurring below about 210° C. Interestingly, when ethanol is used in the place of GVL, a maximum in C6 concentration was also observed. See FIG. 1D. However, overall C6 concentrations were lower when using 80/20 GVL-to-ethanol, suggesting that ethanol acts as an inhibitor rather than as a promoter for cellulose deconstruction. FIG. 1E is a histogram of the cumulative results using the various solvent systems for comparison purposes.

Figures 5A, 5B:
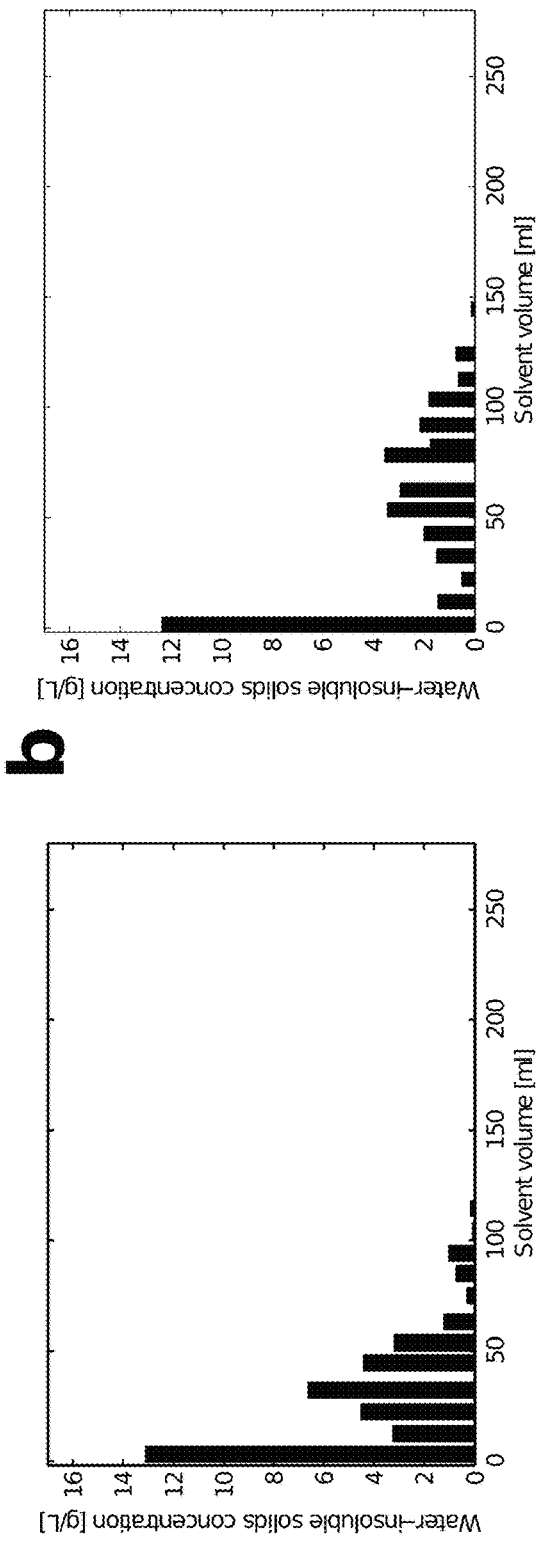
FIGS. 5A and 5B: Fraction concentration results of water-insoluble solids resulting from corn stover extraction in GVL/water mixtures. All solutions contain 5 mM $H_2SO_4$.
Figure 6B:
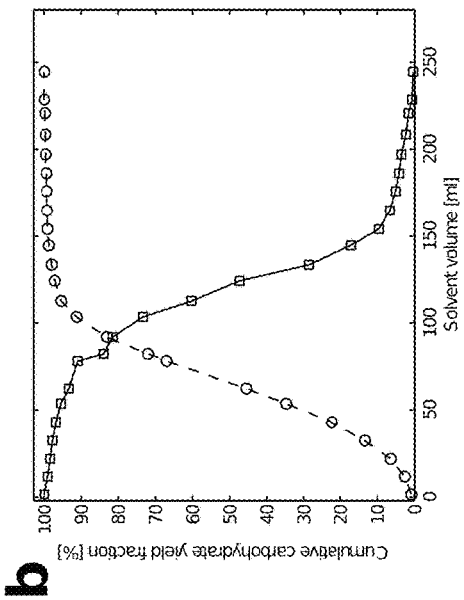
FIGS. 6A, 6B, 6C, and 6D: Cumulative carbohydrate yields as a function of solvent volume. All solvent contained 5 mM $H_2SO_4$. The cumulative xylose yield was calculated from the initial volume to the final volume (0 to 260 ml). The cumulative glucose yield was calculated from the final volume to the initial volume (260 to 0 ml). The intersection between the glucose and xylose cumulative yield curve represents the fractionation volume at which equal portions of the total recoverable sugars can be recovered in separate solvent fractions.
Figure 6D:
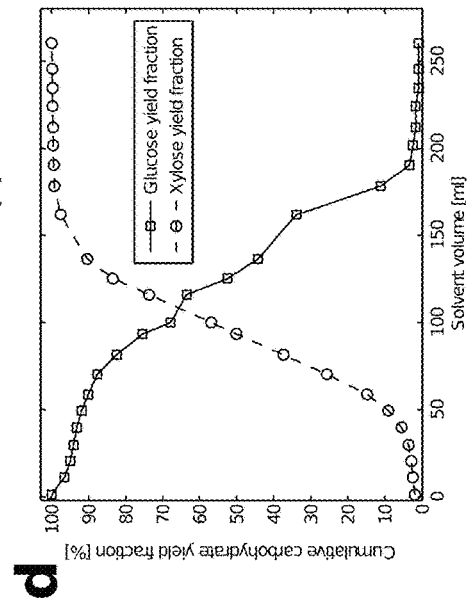
Figure 6A:
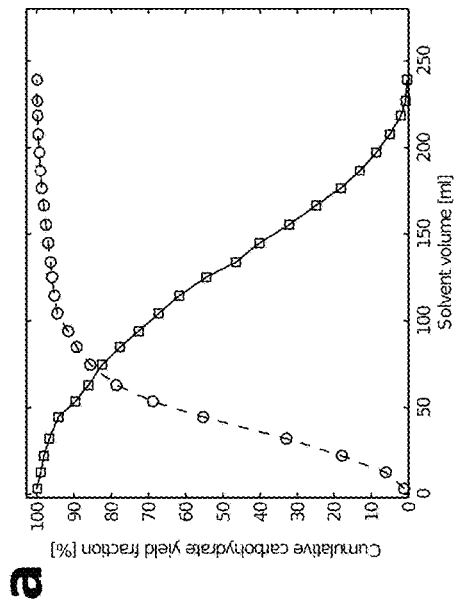
Figure 6C:
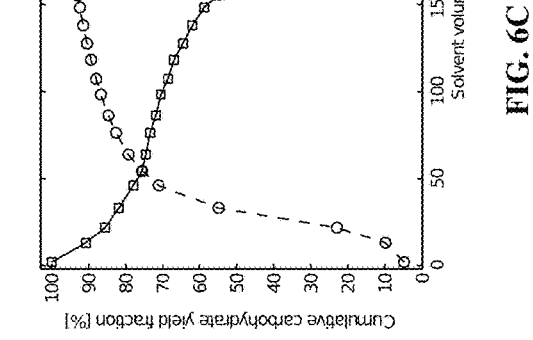

Unlike water or water ethanol mixtures, lactone/water mixtures leave almost no solids in the reactor. The various fractions in GVL/water contain water-insoluble solids, which precipitate when the fraction is diluted with water and which must, according to the mass balance, be comprised mostly of solubilized lignin. The highest concentrations of water-insoluble solids always occurred in the first fraction and are almost absent after the first 10 fractions (see FIGS. 5A and 5B). The total mass of water-insoluble solids corresponded to 95% and 84% of the original lignin mass for extraction with 80/20 wt % and 90/10 wt % GVL-to-water, respectively.

Quantitatively, the lactone/water/dilute acid process leads to an increase in overall C5 sugar recovery by 5-20 percentage points and, notably, to a 2 to 4-fold increase (200% to 400% increase) in C6 sugar recovery. See FIG. 1E. Also notable is that yields for both C5 sugars and C6 sugars are almost identical for maple wood as compared to corn stover. Again, see FIG. 1E. This indicates that carbohydrate recovery is independent of the type of substrate used. Furthermore, due to the fractionation concentration profile, the C6 and C5 sugars are better resolved when using the lactone/water solvent system. Despite the increased amount of sugars associated with the GVL/water mixtures, over 80% of both extracted C5 and C6 sugars can be recovered in separate solvent fractions, as contrasted to 75% for water and 65% for ethanol. (These percentages were calculated as illustrated in FIGS. 6A through 6D; see the Examples.) The capability to separate the C5 sugars from the C6 sugars enables using the C5 and C6 fractions in separate and distinct upgrading processes. In addition, given the carbohydrate extraction profile associated with lactone/water systems (i.e., most sugars have been extracted once temperatures around 483-493 K have been reached), carbohydrate concentrations can be increased by decreasing the temperature ramp time without significantly decreasing carbohydrate yields. This is due to reducing the solvent volume flowed through biomass. As shown in FIG. 1F, soluble carbohydrate yields decrease by less than 4% when the temperature ramp time is shortened from 2 hr to 1 hr.

Shortening the temperature ramp time to 30 min decreases soluble carbohydrate yield by less than 10 percentage points (as compared to a 2 hr ramp time).

The data presented in FIGS. 1A through 1F show that the lactone/water/dilute acid system promotes cellulose and hemicellulose hydrolysis as contrasted to traditional solvents such as water and water/ethanol mixtures. An important feature of GVL/water solvent systems is that the aqueous phase can be separated from the GVL by addition of salt[16]. In FIGS. 2A, 2B, and 2C, carbohydrate recovery in the aqueous phase is shown as a function of NaCl content. (NaCl is exemplary. Any non-reactive salt or solute that drives partitioning of the product mixture into an aqueous layer and an organic layer that contains most of the lactone may be used.) Using simulated carbohydrate feeds in GVL/water mixtures, the data show that there was a tradeoff between obtaining higher aqueous concentrations of carbohydrates at low levels of NaCl addition (e.g., 4% aq) and increased recovery of carbohydrates in the aqueous phase at higher salt levels (10-12% aq). See the Examples for full details. This tradeoff is illustrated in FIGS. 2A, 2B, and 2C for feeds derived from corn stover. When recovering 40-50% of the sugars in the aqueous phase, the glucose and xylose concentrations can be increased by about 10- to 20-fold for 80/20 GVL/water and 90/10 GVL/water, respectively. The highest carbohydrate concentrations (over 110 g/L) are within range of the highest concentrations obtained without any drying from pretreatment and enzymatic hydrolysis, which range between 150 and 200 g/L depending on the substrate and enzyme loading[17,18]. When 80-90% and 60% of the sugars are recovered in the aqueous phase from 80/20 GVL/water and 90/10 GVL/water, carbohydrate concentration drops to 25 g/L and 60 g/L, respectively. See FIG. 2A for the 80/20 data and FIG. 2B for the 90/10 data. Furthermore, concentrations can easily be increased by removing the first and last fractions from the flow-through process which contained very few sugars. As shown in FIG. 2C, while conserving the fractions that still contain 97% of both C5 and C6 sugars, carbohydrate concentrations can be increased from 25 g/L to 33 g/L simply by discarding low concentration fractions in the 80/20 GVL fractionation product. This 33 g/L solution was used in carbohydrate upgrading experiments to monomers and furans, discussed below.

As discussed earlier, carbohydrate concentrations can also be increased by shortening the temperature ramp time. As shown in FIG. 2C, using 80/20 GVL and a 12% aq NaCl content, carbohydrate concentrations increase to 48 g/L and 72 g/L with a 1 hr and 30 min temperature ramp respectively, with recovery efficiencies of around 90% and 80%.

Recovery was slightly reduced in biomass derived feeds compared to simulated feeds composed of monosaccharides. See FIGS. 7A and 7B, and the Examples. This was mainly due to oligomers partitioning more readily in the organic phase than monomers. In addition, NaCl proved to be less soluble in biomass-derived feeds with saturation in 90/10 GVL occurring between about 10 and 12% aq, while NaCl saturation occurred at about 16% aq in the simulated feeds.

Figures 3A, 3B:
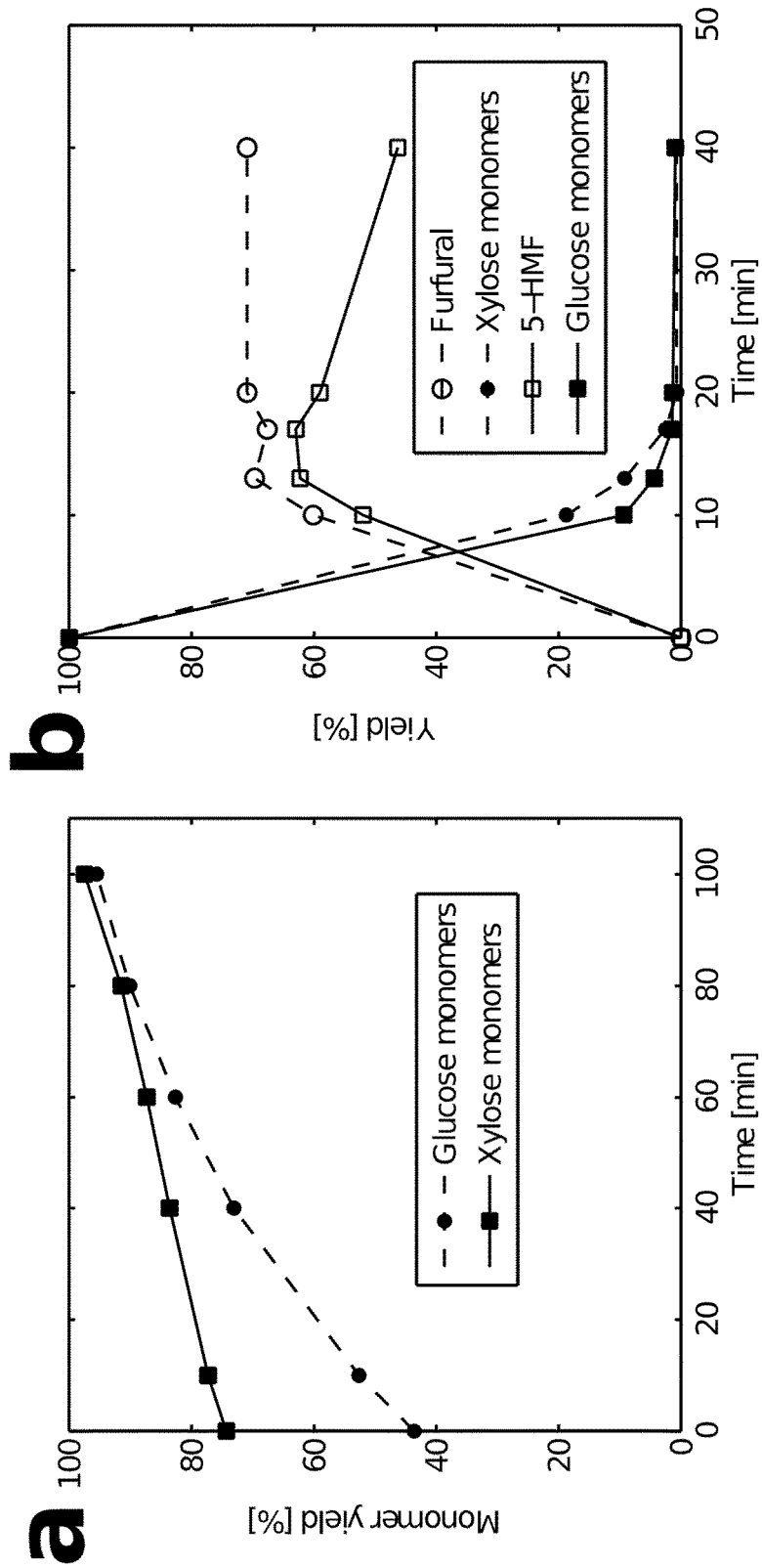
FIGS. 3A and 3B: Carbohydrate upgrading.

As shown in FIGS. 2A, 2B, and 2C, the carbohydrates recovered in the aqueous phase are a mixture of monomers and oligomers. For biological upgrading, monomers are preferable starting products, especially compared to oligomers with a degree of polymerization greater than two. However, because most of the acid catalyst is recovered in the separated aqueous phase (when using homogeneous acid catalysts such as mineral acids), it offers an acidic aqueous environment that is well suited to oligomer depolymerization[19]. The data in FIG. 3A show that by heating the unmodified aqueous phase separated from the 80/20 GVL product stream, over 95% of total C5 sugars and C6 sugars can be recovered in the form of monomers after treatment at about 140° C. for 100 min. These monosaccharrides are ideal substrates for biological upgrading.

Carbohydrates can also be upgraded to useful fuels and chemicals through the furan platform[20-22]. Xylose and glucose can undergo dehydration to furfural and 5-hydroxymethyl-furfural (5-HMF), respectively. Both of these species are unstable at high temperatures in acidic environments and benefit from the continuous extraction in an organic phase such as 2-sec-butyl-phenol (SBP) during reaction[23]. Furthermore, selectivity to 5-HMF from glucose is greatly improved after glucose is isomerized to fructose, which can be catalyzed with a Lewis acid such as $AlCl_3$[23]. Phase modifiers such as NaCl, further promote 5-HMF production by modifying their partition coefficient to the organic phase[21-23].

In FIG. 3B, furfural and 5-HMF yields are shown as a function of reaction time at 170° C. from the soluble carbohydrates (monomers and oligomers) recovered from the 80/20 GVL separated aqueous phase. This phase was used unmodified except for the addition of $AlCl_3$ and the presence of the SBP organic phase. Yields above 60 and 70% for 5-HMF and furfural, respectively are almost identical to those obtained from glucose and xylose despite the presence of oligomers and other biomass by-products[23,24].

Because of the moderate conditions used to produce these sugars and the demonstrated versatility of these biomass-derived carbohydrates (suitable for both biological and chemical upgrading), this present method can be used in any number of biofuel and bioproduct production processes that use glucose, xylose or water-soluble oligomers comprising glucose and/or xylose as reactant or reagent.

Examples

The following Examples are included solely to provide a more thorough disclosure of the method described and claimed herein. The Examples do not limit the scope of the claimed method in any fashion. The Examples provide the experimental methods by which the results presented in FIGS. 1A-1F, 2A-2C, 3A, 3B, 5A, 5B, 6A-6D, 7A, and 7B were obtained.

Flow-Through Reactor:

A schematic of the flow-through reaction system used in the Examples is shown in FIG. 4. Corn stover was obtained through the Great Lakes Bioenergy Research Center (GL-BRC, Madison, Wis.) and maple wood was obtained from Mascoma (Hanover, N.H.). Their compositions are given in Table 1.

TABLE 1

| Biomass composition | | | |
|---|---|---|---|
|  | Glucan [wt %] | Xylan [wt %] | Klason lignin [wt %] |
| Corn stover | 35.10 | 22.20 | 16.20 |
| Maple wood | 41.90 | 19.30 | 24.90 |

Approximately 2.5 g of biomass were mixed with 5 g of silicon dioxide fused granules (Sigma-Aldrich, St. Louis, Mo.) and placed into the heated zone of the flow-through reactor between two beds of pure silicon dioxide granules separated by quartz wool plugs (Grace-Davison, Albany, Oreg.). See FIG. 4. The reactor's heated zone is fitted between two aluminum blocks placed within an insulated furnace (Applied Test Systems, Butler, Pa.). A type-K thermocouple (Omega Engineering, Inc. Stamford, Conn.) was placed at the reactor wall and was used to monitor and control the reactor temperature using a 16A series controller (Love Controls, a division of Dwyer Instruments, Inc., Michigan City, Ind.). Solvent was flowed through the system using an HPLC pump as shown at the top of FIG. 4 (Lab Alliance-brand Series I, Thermo-Fischer Scientific, Waltham, Mass.). Pressure was maintained constant at 300 psi by flowing helium (Airgas, West Chicago, Ill.) in the headspace of the liquid collector through a back-pressure regulator (1500 psi, 10.3 MPa, Tescom, a wholly owned subsidiary of Emerson Process Management, Elk River, Minn.). At the start of the reaction, dry biomass was heated to 423 K in the presence of helium using a 20 min ramp. The temperature was allowed to equilibrate between 423 and 433 K for 3 min after which solvent was flowed through the biomass at a rate of 2 ml/min while a 2 hr temperature ramp was applied between 433 and 493 K. The resulting flow-through liquid was sampled approximately every 5 min by draining the liquid collector.

Aqueous Phase Separation:

A given amount sodium chloride (Sigma-Aldrich) was added to the liquids resulting from flow-through experiments using GVL-$H_2O$ mixtures as a solvent in order to separate the aqueous phase. The resulting solutions were repeatedly shaken and sonicated in a sonication bath (FS28, Fisher-Scientific) until no solids were visible. The mixtures were then centrifuged at 4500 rpm for 4 min in a Sorvall ST16 centrifuge (ThermoFisher). The heavier aqueous phase was removed using a syringe and needle to measure its mass, after which both phases were analyzed.

Monomer Production:

Oligomer depolymerization reactions were carried out in thick-walled glass reactors (5 mm, Supelco, a subsidiary of Sigma-Aldrich, Bellefonte, Pa.) with a magnetic stirrer. Approximately 2.5 g of unmodified aqueous solutions resulting from the aqueous phase separation were placed in the reactors. The glass reactors were heated and stirred using an oil bath at 413 K placed an Isotemp digital stirring hotplate set at 800 rpm (Fisher Scientific). Reactors were stopped at specific reaction times by placing the reactors in an ice slurry.

Furan Production:

Aqueous solutions (1.5 g each) resulting from the aqueous phase separation to which 100 mM of $AlCl_3$ (Sigma-Aldrich) was added, were contacted with 3 g of 2-sec-butyl-phenol (Alfa-Aesar, a Johnson Matthey Company, Ward Hill, Mass.) in a 10 ml thick-walled glass reactor (Grace Davison). To begin each reaction, the resulting mixture was placed in an oil bath heated with an Isotemp digital stirring hotplate (Fisher Scientific). The hotplate was used to stir a magnetic stir bar in the reactor at 1200 rpm. In the same fashion as in the monomer production experiments, reactors were cooled at specific reaction times by placing them in an ice slurry.

Analytical Methods:

Aqueous phase, GVL/water and ethanol/$H_2O$ were analyzed for glucose, xylose, 5-hydroxymethylfurfural (HMF) and furfural and after 10× dilution in water using a Waters 2695 HPLC system with a Bio-Rad Aminex HPX-87H column and a 5 mM $H_2SO_4$ aqueous mobile phase flowing at 0.6 ml/min (Waters, Inc., Milford, Mass.; Bio-Rad Laboratories, Inc., Hercules, Calif.). The 2-sec-butyl-phenol phase was analyzed using a Waters 2695 HPLC system with a Zorbax SB-C18 5 μm column (Agilent, Santa Clara, Calif.)

using 5 mM H$_2$SO$_4$ as the aqueous phase with acetonitrile as the organic modifier. Both systems were equipped with a RI 2414 (refractive index) detector and a PDA 960 (photodiode array) detector (Waters). Sugars were measured using the RI detector while 5-HMF and furfural were measured using the PDA detector at 320 and 230 nm respectively. Oligomers were measured according to the procedure published by the National Renewable Energy Laboratory[19] using unstirred 10 ml thick-walled glass reactors (Grace-Davison) placed in an oil bath set to 121° C.

Water insoluble solids in GVL/water fractions were measured by diluting the solutions 10 times using water and filtering the resulting mixture using a 0.2 µm nylon filter (Millipore, Billerica, Mass.). The filter was dried overnight in a vacuum oven (Fisher-Scientific) set at 333 K and weighed for recovered solids.

Figures 7A, 7B:
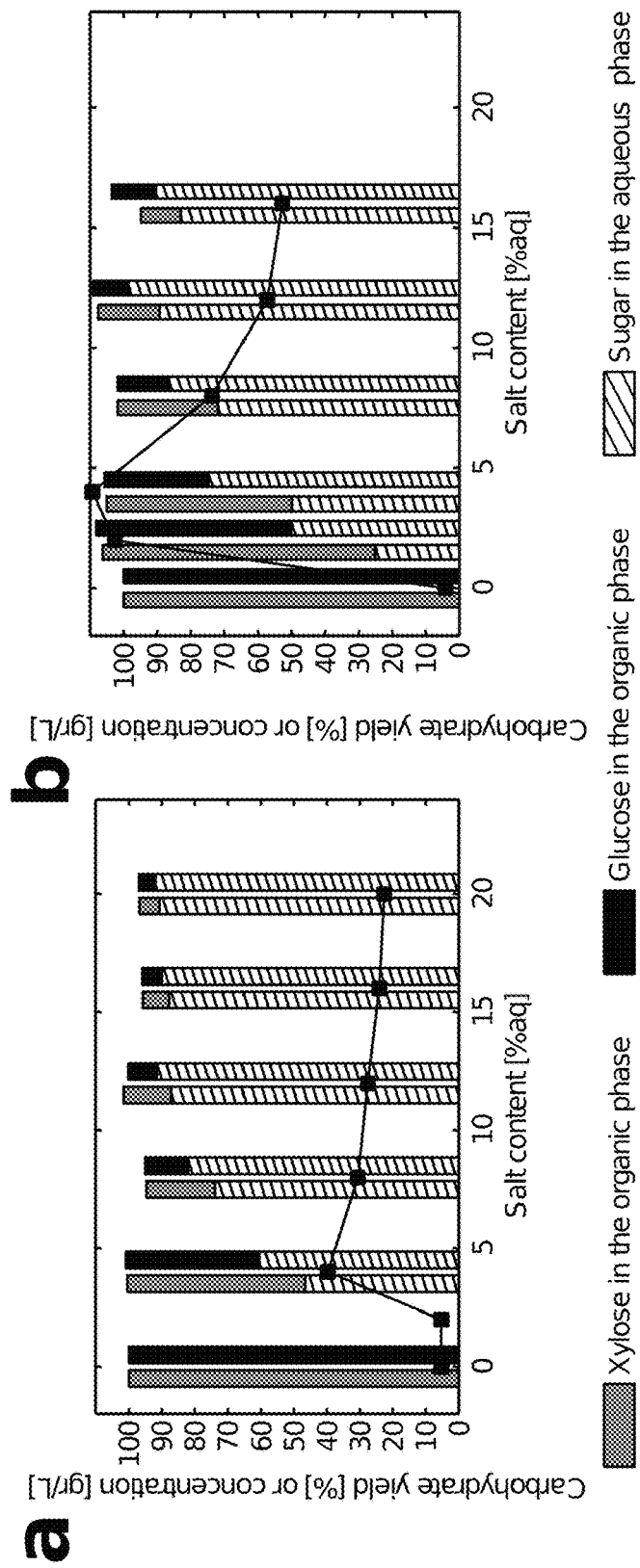
FIGS. 7A and 7B: Aqueous phase separation and carbohydrate recovery from simulated carbohydrate feeds in GVL mixtures using NaCl. Salt content is given as the mass fraction of the total amount of water present. Stacked bars represent fractions of the total carbohydrate yield. The solid line represents the total mass concentration of sugars in solution.

Aqueous Phase Separation Optimization:

Two simulated feeds (80 wt % GVL to 20 wt % water and 90 wt % GVL to 10 wt % water) were constructed based on corn stover fractionation results. Given amounts of glucose and xylose, equivalent to the amounts of their equivalent monomer and oligomer concentrations in the solutions derived from corn stover were added to the respective solvent. The effect of increasing NaCl concentrations on the aqueous phase separation is shown in FIGS. 7A (80 wt % GVL/20 wt % water) and 7B (90 wt % GVL/10 wt % water). The solution containing 80 wt % GVL showed salt saturation at between 16 and 20% aq (i.e., mass fraction with respect to the total amount water present) NaCl while the solution containing 90 wt % GVL showed saturation between 12 and 16% aq NaCl.

REFERENCES CITED

The following documents are incorporated herein by reference.
1. Somerville, C. The Billion-Ton Biofuels Vision. *Science* 312, 1277 (2006).
2. Sanderson, K. Lignocellulose: A chewy problem. *Nature* 474, S12 (2011).
3. Ragauskas, A. J. et al. The Path Forward for Biofuels and Biomaterials. *Science* 311, 484-489 (2006).
4. Lynd, L. R. et al. How biotech can transform biofuels. *Nat. Biotech.* 26, 169-172 (2008).
5. Von Sivers, M. & Zacchi, G. A techno-economical comparison of three processes for the production of ethanol from pine. *Bioresource Technology* 51, 43-52 (1995).
6. Wilson, D. B. Cellulases and biofuels. *Current opinion in biotechnology* 20, 295-299 (2009).
7. Houghton, J. *Breaking the biological barriers to cellulosic ethanol: A joint research agenda.* (US Department of Energy, 2005).at <http://www.doegenomestolife.org/biofuels>
8. Binder, J. B. & Raines, R. T. Fermentable sugars by chemical hydrolysis of biomass. *Proceedings of the National Academy of Sciences* 107, 4516-4521 (2010).
9. Bobleter, O. Hydrothermal Degradation Of Polymers Derived From Plants. *Progress In Polymer Science* 19, 797-841 (1994).
10. Peterson, A. A. et al. Thermochemical biofuel production in hydrothermal media: A review of sub- and supercritical water technologies. *Energy Environ. Sci.* 1, 32-65 (2008).
11. Shill, K. et al. Ionic liquid pretreatment of cellulosic biomass: Enzymatic hydrolysis and ionic liquid recycle. *Biotechnology and Bioengineering* 108, 511-520 (2011).
12. Lee, Y. Y., Iyer, P. & Torget, R. W. in *Recent Progress in Bioconversion of Lignocellulosics* (Tsao, P. D. G. T. et al.) 93-115 (Springer Berlin Heidelberg, 1999).at <http://link.springer.com/chapter/10.1007/3-540-49194-5_5>
13. Liu, C. G. & Wyman, C. E. The effect of flow rate of very dilute sulfuric acid on xylan, lignin, and total mass removal from corn stover. *Industrial & Engineering Chemistry Research* 43, 2781-2788 (2004).
14. Gürbüz, E. I. et al. Conversion of Hemicellulose into Furfural Using Solid Acid Catalysts in γ-Valerolactone. *Angewandte Chemie International Edition* n/a-n/a (2012).doi:10.1002/anie.201207334
15. Alonso, D. M., Wettstein, S. G., Mellmer, M. A., Gurbuz, E. I. & Dumesic, J. A. Integrated conversion of hemicellulose and cellulose from lignocellulosic biomass. *Energy Environ. Sci.* (2012).doi:10.1039/C2EE23617F
16. Wettstein, S. G., Alonso, D. M., Chong, Y. & Dumesic, J. A. Production of levulinic acid and gamma-valerolactone (GVL) from cellulose using GVL as a solvent in biphasic systems. *Energy Environ. Sci.* 5, 8199-8203 (2012).
17. Luterbacher, J. S., Chew, Q., Li, Y., Tester, J. W. & Walker, L. P. Producing concentrated solutions of monosaccharides using biphasic CO2-H2O mixtures. *Energy Environ. Sci.* 5, 6990-7000 (2012).
18. Hodge, D. B., Karim, M. N., Schell, D. J. & McMillan, J. D. Soluble and insoluble solids contributions to high-solids enzymatic hydrolysis of lignocellulose. *Bioresour. Technol.* 99, 8940-8948 (2008).
19. Sluiter, A. et al. *Determination of sugars, byproducts, and degradation products in liquid fraction process samples.* (National Renewable Energy Laboratory, 2004).
20. Lange, J.-P., Van der Heide, E., Van Buijtenen, J. & Price, R. Furfural—A Promising Platform for Lignocellulosic Biofuels. *ChemSusChem* 5, 150-166 (2012).
21. Roman-Leshkov, Y., Chheda, J. N. & Dumesic, J. A. Phase modifiers promote efficient production of hydroxymethylfurfural from fructose. *Science* 312, 1933 (2006).
22. Roman-Leshkov, Y., Barrett, C. J., Liu, Z. Y. & Dumesic, J. A. Production of dimethylfuran for liquid fuels from biomass-derived carbohydrates. *Nature* 447, 982-985 (2007).
23. Pagán-Torres, Y. J., Wang, T., Gallo, J. M. R., Shanks, B. H. & Dumesic, J. A. Production of 5-Hydroxymethylfurfural from Glucose Using a Combination of Lewis and Brønsted Acid Catalysts in Water in a Biphasic Reactor with an Alkylphenol Solvent. *ACS Catal.* 2, 930-934 (2012).
24. Gurbuz, E. I., Alonso, D. M., Bond, J. Q. & Dumesic, J. A. Reactive extraction of levulinate esters and conversion to gamma-valerolactone for production of liquid fuels. *ChemSusChem* 4, 357-361 (2011).

What is claimed is:

1. A process to produce an aqueous solution of carbohydrates comprising C6-sugar-containing oligomers, C6-sugar monomers, C5-sugar-containing oligomers, C5-sugar monomers, or any combination thereof, the process comprising:
    reacting biomass or a biomass-derived reactant with a solvent system comprising (i) an organic solvent selected from the group consisting of beta-, gamma-, and delta-lactones, and combinations thereof, and (ii) at least about 1 wt % water; in the presence of an acid catalyst for a time and under conditions to yield a product mixture wherein at least a portion of water-insoluble C6-sugar-containing polymers or oligomers, or water-insoluble C5-sugar-containing polymers or oligomers, if present in the biomass or biomass-derived reactant, are converted to water-soluble C6-sugar-containing oligomers, C6-sugar monomers, C5-sugar-containing oligomers, C5-sugar monomers, or any combination thereof.

2. The process of claim 1, wherein the organic solvent is miscible with water.

3. The process of claim 1, wherein the organic solvent can dissolve from 2 wt % to 40 wt % water.

4. The process of claim 1, wherein the organic solvent is gamma-valerolactone (GVL).

5. The process of claim 1, wherein the organic solvent is present in a mass ratio with water, organic solvent:water, selected from the group consisting of about 60:40, about 65:35, about 70:30, about 75:25, about 80:20, about 85:15, about 90:10, about 95:5, about 97:3, about 98:2, and about 99:1.

6. The process of claim 1, wherein the acid catalyst is homogeneous or heterogeneous, and if the acid catalyst is homogeneous it is present in a concentration not greater than 100 mM based on volume of the solvent system, and if the acid catalyst is heterogeneous it is present in a concentration not greater than 1.0 wt % based on weight of the solvent system.

7. The process of claim 6, wherein the acid catalyst is a mineral acid or an organic acid.

8. The process of claim 6, wherein the acid catalyst is a solid acid catalyst selected from the group consisting of solid Brønsted acid catalysts, solid Lewis acid catalysts, and combinations thereof.

9. The process of claim 8, wherein the solid acid catalyst is a heteropolyacid.

10. The process of claim 8, wherein the solid acid catalyst is an amorphous or mesoporous silica, which may be unfunctionalized or functionalized with acidic modifier.

11. The process of claim 8, wherein the solid acid catalyst is a zeolite.

12. The process of claim 1, conducted at a temperature range selected from the group consisting of from about 100° C. to about 300° C., about 140° C. to about 240° C., and about 150° C. to about 200° C.

13. The process of claim 1, conducted at a dynamic temperature range.

14. The process of claim 13, wherein the dynamic temperature range ramps from a first temperature to a second temperature that is higher than the first temperature.

15. The process of claim 13, wherein the dynamic temperature range changes from a first temperature to a second temperature in a non-linear fashion.

16. The process of claim 1, wherein the biomass or a biomass-derived reactant comprises water-insoluble glucose-containing polymers or oligomers, or water-insoluble xylose-containing polymers or oligomers, or any combination thereof, and these, if present, are converted to water-soluble glucose-containing oligomers, glucose monomers, water-soluble xylose-containing oligomers, xylose monomers, or any combination thereof.

17. The process of claim 1, wherein residence time of the reaction is selected from the group consisting of 1 min to 24 hours, 1 min to 20 hours, 1 min to 12 hours, 1 min to 6 hours, 1 min to 3 hours, 1 min to 2 hours, 1 min to 1 hour, and 1 min to 30 min.

* * * * *